US00PP07775P

United States Patent [19]

Zaiger et al.

[11] Patent Number: Plant 7,775

[45] Date of Patent: Jan. 28, 1992

[54] PEACH TREE "MAY PRIDE"

[76] Inventors: Chris F. Zaiger, 537 Rosemore Ave.; Gary N. Zaiger, 1907 Elm Ave.; Leith M. Gardner, 1207 Grimes Ave.; Grant G. Zaiger, 4005 California Ave., all of Modesto, Calif. 95351

[21] Appl. No.: 513,604

[22] Filed: Apr. 2, 1990

[51] Int. Cl.[5] ..... A01H 5/00

[52] U.S. Cl. ..... Plt./43

[58] Field of Search ..... Plt./43, 41

*Primary Examiner*—Howard J. Locker

[57] ABSTRACT

A new and distinct variety of peach tree with the following unique combination of desirable features.

1. Early maturity of medium size fruit.
2. Fruit with good flavor and eating quality.
3. A low winter chilling requirement of approximately 250 hours, being able to produce in areas with warm winter temperatures.
4. Fruit with firm flesh, good shipping ans storage quality.
5. Vigorous, upright growth.
6. Regular and productive bearer.
7. Fruit with a high degree of attractive red skin color.

ORIGIN OF THE VARIETY

The new variety of peach tree was originated by us in the experimental orchard located near Modesto, Calif. from a cross between two selected seedlings with the identification numbers of 37G804 and 37G870. The female parent 37G804 originated as a selected seedling from a second generation cross between Red Grand Nectarine U.S. Plant Pat. No. 1,060 and Desert Gold Peach (non-patented). The pollen parent 37G870 originated from a cross between Ruby Gold Nectarine U.S. Plant Pat. No. 3,01and a low chilling peach of unknown parentage. Seeds from

1 Drawing Sheet

ASECXAL REPRODUCTION OF THE VARIETY

The present new variety was asexual propagated by budding, as preformed by us in the experimental orchard located near Modesto, Calif., and shows that all characteristics run true to the original tree and are established and transmitted through succeding propagations.

SUMMARY OF THE VARIETY

The new and distinct variety of peach tree is of large size, vigorous upright growth and a regular and productive bearer of medium size, yellow flesh clingstone fruit with good flavor and eating quality. The tree is further characterized by having a low winter chilling requirement of approximately 250 hours, and producing fruit with firmer flesh, greater shipping quality and a higher degree of attractive red skin color than most other early maturing, low chilling peach varieties.

DESCRIPTION OF THE PHOTOGRAPHS

The accompanying photographs show reproductions of typical specimens of the fruit and foliage of the new variety. The upper and lower surface of the leaves being illustrated and the exterior and sectional view of the fruit shown with the fruit divided on its suture plane to reveal flesh coloration and showning a stone remaining in place. The photographs were taken soon after the fruit was picked (firm ripe) and the colors are as nearly true as is reasonably possible in a color representation of this type.

DESCRIPTION OF THE VARIETY

The botanical details of the new and distinct variety of peach tree, its flowers, foliage and fruit are based on observations of the specimens grown near Modesto, Calif., with color terminology (except those in common terms) in accordance with Reinhold Color Atlas by A. Kornerup and J. H. Wanscher.

Tree:
- *Size.*—Large.
- *Vigor.*—Vigorous.
- *Form.*—Upright.
- *Density.*—Medium dense.
- *Shape.*—Usually pruned to vase shape.
- *Productivity.*—Productive.
- Bearer.—Regular.

Trunk:
- *Size.*13 Medium stocky.
- *Texture.*—Medium shaggy.

Branches:
- *Size.*—Medium.
- *Texture.*—Medium rough.
- *Lenticels.*—Medium number. Medium size.
- *Color.*—New growth—reddish brown to light brown. Mature growth—light brown to brown.

Leaves:
- *Size.*—Medium. Average length—5½". Average width—1½".
- *Texture.*—Smooth.
- *Petiole.*—Short to medium length. Medium width.
- *Form.*—Lanceolate. Pointed.
- *Margin.*—Crenate.
- *Glands.*—Globose. Average number 2— number varies from 1 to 3.
- *Color.*—Upper surface—green to dark green (28-F-6) to (28-F-8). Lower surface—grayish green to bracken green (29-E-6) to (29-E-8).

Flower Buds:
- *Size.*—Medium to large.
- *Form.*—Plump.
- *Pubescence.*—Pubescent.

Flower:
- *Size.*—Large and showy.

*Blooming period.*—Date of first bloom: Feb. 21, 1988. Date of last bloom: Feb. 25, 1988. Varies slightly with climatic conditions.

*Pollen.*—Present.

*Color.*—Pink.

Fruit:

*Maturity when described.*—Firm ripe.

*Date of first picking.*—May 23, 1988.

*Date of last picking.*—May 28, 1988.

*Size.*—Medium. Average diameter axially—2½". Average transversely in suture plane—2½".

*Form.*—Globose—nearly symmetrical.

*Suture.*—Shallow—extends from base to apex.

*Apex.*—Rounded to slightly retuse.

*Base.*—Retuse.

*Cavity.*—Rounded to slightly elongated in suture plane. Average depth—7/16". Average breadth—¾".

Flesh:

*Ripens.*—Uniform.

*Texture.*—Firm.

*Fiber.*—Few, tender.

*Juice.*—Moderate.

*Flavor.*—Mild, good balance between sugar and acid.

*Aroma.*—Moderate.

*Eating quality.*—Good.

*Color.*—Yellow to dark yellow—(4-A-7) to (4-A-8).

Skin:

*Thickness.*—Medium.

*Texture.*—Medium—tenacious to flesh.

*Tendency to crack.*—None.

*Down.*—Moderate—medium length.

*Color.*—Bright yellow ground color—(4-A-8) to (5-A-7). Overspread with red—(9-A-8) to (9-B-8).

Stone:

*Type.*—Clingstone.

*Size.*13 Medium to large. Average length — 1⅛". Average width — ⅞". Average thickness — ½".

*Form.*—Ovid.

*Base.*—Mostly straight — some rounded.

*Apex.*—Acuminate.

*Sides.*—Equal to unequal.

*Surface.*—Furrowed toward apex, pitted toward base.

*Ridges.*—Rounded.

*Tendency to split.*—Slight.

*Color.*—Light brown to brown — (8-B-4) to (8-C-6).

Use: Dessert

*Market.*—Local and long distance.

Keeping quality: Good.

Shipping quality: Good.

The new variety of peach tree, its flower and fruit herein described may vary in slight detail due to climatic, soil conditons and cultural practices under which the variety may be grown. The present detailed description is that of the variety grown under the ecological conditions prevailing near Modesto , Calif.

The following is claimed:

1. A new and distinct variety of peach tree, substantially as illustrated and described, characterized by its large size, vigorous upright growth, and a regular and productive bearer of medium size, early maturing, yellow flesh, clingstone fruit with good flavor and eating quality; the tree is further characterized by having a low winter chilling requirement of approximately 250 hours and producing firmer fruit with a higher degree of attractive red skin color than most other early maturing peach varieties with a low winter chilling requirement.

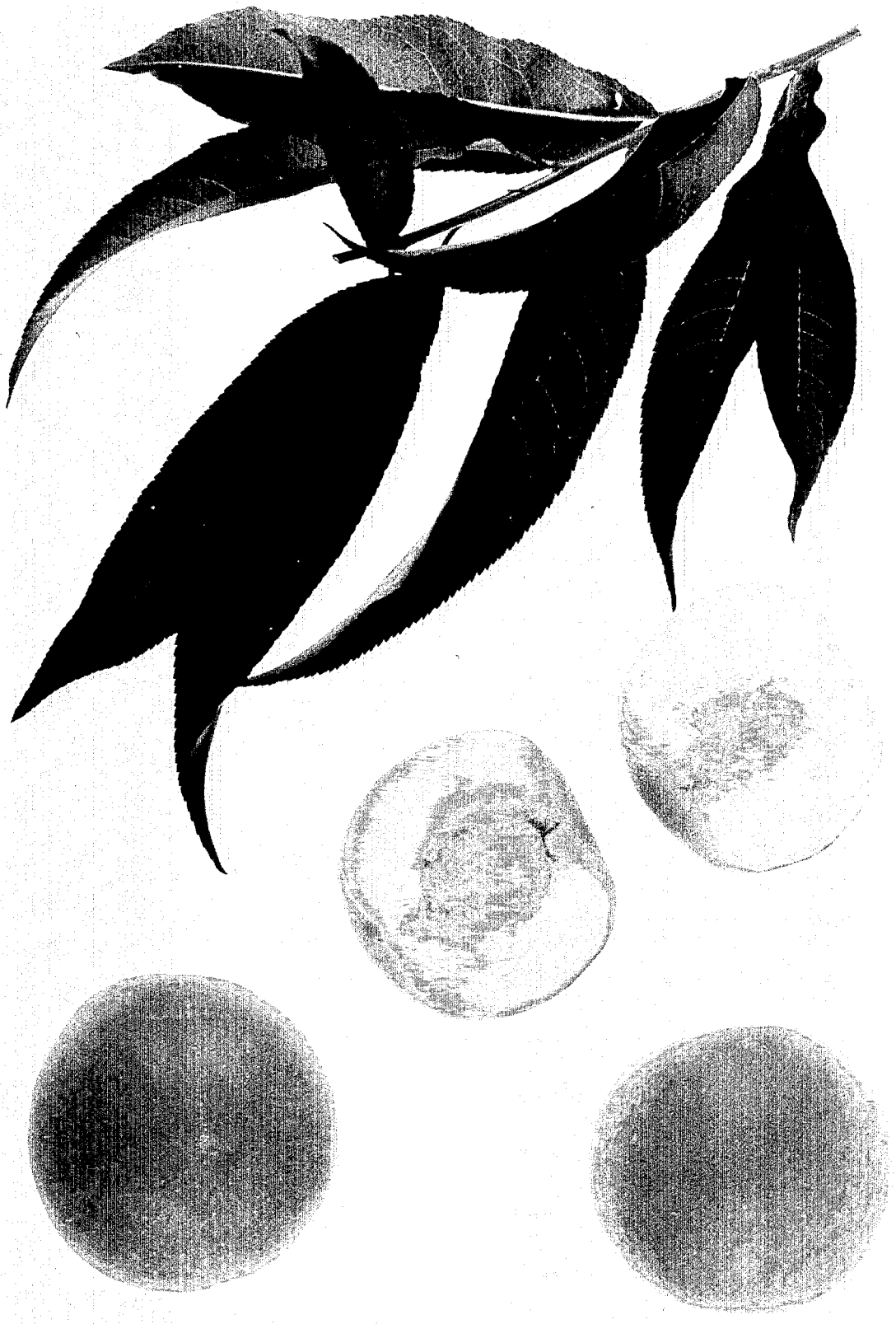

* * * * *